United States Patent [19]

Sheth et al.

[11] 4,137,300

[45] Jan. 30, 1979

[54] SUSTAINED ACTION DOSAGE FORMS

[75] Inventors: Pravin Sheth, Springfield; Lewis J. Leeson, Roseland, both of N.J.

[73] Assignee: Ciba-Geigy Corporation, Ardsley, N.Y.

[21] Appl. No.: 806,424

[22] Filed: Jun. 14, 1977

Related U.S. Application Data

[63] Continuation-in-part of Ser. No. 716,314, Aug. 20, 1976, abandoned.

[51] Int. Cl.$^2$ .......................... A61K 9/24; A61K 9/38; A61K 9/42
[52] U.S. Cl. ....................................... 424/21; 424/19; 424/36; 424/38
[58] Field of Search .................................. 424/19–22, 424/36, 38

[56] References Cited

U.S. PATENT DOCUMENTS

| 874,310 | 12/1907 | Donard et al. | 424/36 |
| 2,895,880 | 7/1959 | Rosenthal | 424/359 |
| 3,062,720 | 11/1962 | Costello | 424/22 |
| 3,079,303 | 2/1963 | Raff et al. | 424/36 |
| 3,108,046 | 10/1963 | Harbit | 424/38 |
| 3,147,187 | 9/1964 | Playfair | 424/36 |
| 3,184,386 | 5/1965 | Stephenson | 424/21 |

Primary Examiner—Shep K. Rose
Attorney, Agent, or Firm—Theodore O. Groeger

[57] ABSTRACT

By incorporating solid drug substances into mixtures of higher alkanols and/or alkanoic acids melting above 25° C., forming granules thereof and covering them with a prolamine, a pharmaceutical dosage form is obtained, which slowly and evenly releases the drug within the gastrointestinal tract of a mammal.

13 Claims, No Drawings

SUSTAINED ACTION DOSAGE FORMS

CROSS-REFERENCE TO RELATED APPLICATION

This is a continuation-in-part of application Ser. No. 716,314, filed Aug. 20, 1976 (now abandoned).

BACKGROUND OF THE INVENTION

It is known that higher alkanols and/or alkanoic acids are useful ingredients of pharmaceutical dosage forms, either in regular tablets or in the core material of sustained release coated products. Prolamines are also known as edible coatings of food stuffs and pharmaceutical preparations, either in tablets, or smaller particles. Said materials are often utilized with other ingredients to make up highly complex mixtures, but have never been reported in the combination described below. Surprisingly it was found that the combination of said 3 or 4 basic ingredients alone results in well reproducible, sustained action dosage forms, the drug-release of which can be easily controlled by varying the relative proportions of said constituents, so that release times from about 8 to 24 hours can be achieved.

SUMMARY OF THE INVENTION

The present invention concerns and has for its object the provision of (1) a new sustained action dosage form comprising: (a) a core-mixture of a pharmacologically effective substance and at least two members selected from a higher alkanol and alkanoic acid melting above 25° C. and (b) an outer layer of a prolamine, as well as (2) a new process for the preparation of sustained release dosage forms, which consists in (c) mixing a pharmacologically effective substance with at least two members selected from a higher alkanol and alkanoic acid melting above 25° C.; if desired, heating the mixture to about 55–65° C., (d) granulating the resulting solid mixture with a solution of a prolamine, (e) evaporating the solvent of said solution and, (f) filling the resulting granules into capsules, or compressing them into tablets, if desired, with the use of other components, such as diluents, lubricants and/or disintegrating agents.

DESCRIPTION OF THE PREFERRED EMBODIMENTS

The pharmacologically effective substance is preferably a solid, also melting above 25° C., and may be either an acid or a base, but preferably a neutral substance, such as a salt.

A higher alkanol is preferably a straight chain primary alkanol with 14 to 24 carbon atoms, advantageously cetyl and stearyl alcohol, or various mixtures thereof, especially cetostearyl alcohol, which is an intimate mixture of at least 24% of cetyl alcohol and at most 76% of stearyl alcohol, but also such up to about 50% of cetyl and stearyl alcohol each. A higher alkanoic acid is also preferably a straight chain fatty acid with 14 to 24 carbon atoms, such as myristic, palmitic and/or stearic acid. A mixtures of said alcohols and acids may be used, or natural mixtures obtained from corresponding fats or waxes.

The prolamines are simple, globular proteins, preferably those obtained from grains, advantageously zein, but also gliadin and/or hordenin.

The proportions of drug substance:alcohol/acid:prolamine may vary from about 100:5:3 to about 100:200:80, for tablets preferable from about 100:17:4 to about 100:26:8, especially 100:22:6, and for capsules preferably from about 100:25:5 to about 100:35:7, especially 100:30:6. This mixture may contain additional components in order to become manageable for tabletting or capsule-filling. Said compounds are, for example diluents, such as sugars, e.g. lactose or sucrose; mannitol, cellulose, starches or calcium phosphates; or lubricants, such as alkaline earth metal salts of higher fatty acids, advantageously magnesium stearate, silica, talcum, polyethyleneglycol, teflon or vegetable fats; or disintegrating agents, such as sodium carboxymethylstarch, other starches, alginic acid, its alkali metal salts or surface active agents, e.g. sodium lauryl sulfate. The amount of said additional components ranges from about 0.5 to 100%, preferably about 2 to 50% of the drug substance.

All the above-mentioned substances are utilized in the form of fine powders, passing sieves with openings of about 0.5 to 1.5 mm. The mixture according to (1a) is ground again and should pass through sieves with openings of about 1 to 2 mm.

In the process liquid under item (2) said drug substance and the higher alkanol or alkanoic acid can either be mixed in the form of said fine solid powder, or they are fused together, or one component is dissolved in the lower melting other component, e.g. at about 60° C. The resulting mixture is cooled and ground, if necessary, in order to obtain particles in the range between about 0.5 and about 3 mm each. They are granulated with said prolamine solution, the solvent of which is preferable a mixture of an aqueous lower alkanol and/or alkanone, advantageously ethanol or acetone, and a halogenated lower alkane, e.g. a lower alkylene chloride, advantageously methylene chloride, for example, in the proportions water:alkanol:alkylene chloride between about 1:9:10 to about 1:10:15. Said solution is gradually poured onto the former mixture so that its particles receive an outer layer of the dissolved prolamine.

The resulting wet granulate is dried in a suitable dryer, preferably between about 25 and 30° C., the dried granules blended with said lubricant and milled through a comminuting machine, if necessary.

The resulting granulate according to the invention can either be compressed into tablets, if necessary with an additional amount of lubricant, e.g. magnesium stearate, or the tablets are broken down by a comminuting machine or any suitable grinding equipment, fitted with a screen with openings preferably between 0.5 and 2 mm, and filled into hard gelatin capsules, or said granulate is filled into capsules, preferably hard gelatin capsules, as such, or in admixture with more lubricants and/or fillers, for example, silica, talcum, starches, sugars, cellulose or sodium carboxy-methyl-starch.

The resulting tablets may be conventionally film or sugar coated, either for stability or aesthetic purposes. The following examples illustrate the invention and are not to be construed as being limitations thereof. Temperatures are given in degrees Centigrade and all parts, wherever given, are parts by weight.

Example 1

Preparation of 2,000,000 tablets each containing 100 mg of drug substance:

| Formula: | |
|---|---|
| Tripelennamine hydrochloride | 200.00 kg |

-continued

| Formula: | |
|---|---|
| Cetostearyl alcohol | 44.00 kg |
| Zein | 12.00 kg |
| Magnesium stearate | 6.00 kg |
| Anhydrous ethanol | 22.22 kg |
| Methylene chloride | 22.22 kg |
| Purified water | 2.77 kg |

Procedure:

The drug substance is passed through a screen with openings of about 0.5-1.5 mm to break up any lumps. It is then mixed with cetostearyl alcohol and heated until the powders fuse and form granules at about 55°-65°. The granules are cooled and passed through a comminuting machine and screened through openings of about 1-2 mm. The zein is suspended in the aqueous ethanol and the methylene chloride is added while mixing. The resulting solution is poured onto said granules, using suitable granulating equipment. The wet granulate is dried overnight at about 30°, blended with about half the magnesium stearate, the whole milled through a comminuting machine and passed through a screen with about 0.5-2 mm openings. The granulate is mixed with the balance of the magnesium stearate and compressed into 131 mg tablets using 7.1 mm tooling.

Example 2

Preparation of 100,000 capsules each containing 100 mg of drug substance:

| Formula: | |
|---|---|
| Hydrochlorothiazide | 10.00 kg |
| Cetostearyl alcohol | 3.00 kg |
| Zein | 0.60 kg |
| Magnesium stearate | 0.25 kg |
| Anhydrous ethanol | 1.62 kg |
| Methylene chloride | 1.80 kg |
| Purified water | 0.18 kg |
| Sodium carboxymethyl-starch | 1.00 kg |
| Silica | 0.05 kg |

Procedure:

The drug substance, cetostearyl alcohol and part of the magnesium stearate are mixed for 3 minutes and heated to 55°-65° to form granules. They are cooled to 25°-30° and granulated with the zein solution in the aqueous ethanolmethylene chloride. The granulate is dried overnight at 30°, comminuted and passed through a screen with 2-3 mm openings. The resulting powder is mixed with 0.1 kg of magnesium stearate for 5 minutes and compressed into 2.65 g slugs of 7.2 mm thickness. They are broken in a comminuting machine, passed through a screen with 1 mm openings and the powder blended with the remaining magnesium stearate, sodium carboxymethyl-starch and silica for 10 minutes. 149 mg of the resulting mixture is filled in hard gelatin capsules, using a capsule filling machine.

Example 3

Preparation of 2,500,000 tablets each containing 50 mg of drug substance:

| Formula: | |
|---|---|
| Tripelennamine hydrochloride | 125.00 kg |
| Lactose anhydrous | 67.50 kg |
| Cetostearyl alcohol | 50.00 kg |
| Zein | 12.50 kg |
| Magnesium stearate | 7.50 kg |
| Anhydrous ethanol | 27.00 kg |
| Methylene chloride | 25.00 kg |

-continued

| Formula: | |
|---|---|
| Purified water | 3.00 kg |

Procedure:

According to Example 1, except that 105 mg tablets are compressed, using 6.3 mm tooling.

EXAMPLE 4

Preparation of 2,500,000 tablets each containing 10 mg of drug substance:

| Formula: | |
|---|---|
| Methylphenidate hydrochloride | 25.00 kg |
| Lactose | 205.00 kg |
| Cetostearyl alcohol | 40.00 kg |
| Zein | 12.50 kg |
| Magnesium stearate | 5.00 kg |
| Anhydrous ethanol | 33.75 kg |
| Methylene chloride | 18.75 kg |
| Purified water | 3.75 kg |

Procedure:

According to Example 1, except that 115 mg tablets are compressed, using 6.3 mm tooling.

Example 5

Preparation of 2,000,000 tablets each containing 20 mg of drug substance:

| Formula: | |
|---|---|
| Methylphenidate hydrochloride | 40.00 kg |
| Cetostearyl alcohol | 40.00 kg |
| Lactose | 184.00 kg |
| Zein | 12.00 kg |
| Magnesium stearate | 4.00 kg |
| Anhydrous ethanol | 32.40 kg |
| Methylene chloride | 18.00 kg |
| Purified water | 3.60 kg |

Procedure:

According to Example 1, except that 140 mg tablets are compressed, using 7.1 mm tooling.

Example 6

Preparation of 1,000,000 tablets each containing 160 mg of drug substance:

| Formula: | |
|---|---|
| Oxprenolol hydrochloride | 160.00 kg |
| Lactose anhydrous | 30.00 kg |
| Cetostearyl alcohol | 10.00 kg |
| Zein | 6.00 kg |
| Magnesium stearate | 4.00 kg |
| Anhydrous ethanol | 16.20 kg |
| Methylene chloride | 9.00 kg |
| Purified water | 1.80 kg |

Procedure:

According to Example 1, except that 237 mg tablets are compressed, using 8.7 mm tooling.

In said Examples 3 to 6, the drug substance is mixed first with the lactose and the resultant mixture is processed as the tripelennamine hydrochloride, shown in Example 1 herein.

We claim:

1. A sustained action dosage form of the type comprising at least (a) a core-mixture of a pharmacologically effective substance and at least two members selected from a higher alkanol and alkanoic acid melting above 25° C. and (b) an outer layer of a prolamine, wherein the proportions of said effective substance: said alkanol/acid: said prolamine vary from about 100:5:3 to about 100:200:80.

2. A dosage form as claimed in claim 1, wherein the pharmacologically effective substance is a solid.

3. A dosage form as claimed in claim 1, wherein the higher alkanol is a straight chain primary alkanol with 14 to 24 carbon atoms.

4. A dosage form as claimed in claim 3, wherein the higher alkanol is cetyl or stearyl alcohol, or various mixtures thereof.

5. A dosage form as claimed in claim 1, wherein the higher alkanoic acid is a straight chain fatty acid with 14 to 24 carbon atoms.

6. A dosage form as claimed in claim 5, wherein the higher alkanoic acid is myristic, palmitic or stearic acid, or various mixtures thereof.

7. A dosage form as claimed in claim 4, wherein cetostearyl alcohol is used as alkanol mixture, containing about 24 to 50% of cetyl alcohol and about 76 to 50% of stearyl alcohol.

8. A dosage form as claimed in claim 1, wherein the prolamine is a globular protein obtained from grains.

9. A dosage form as claimed in claim 8, wherein the prolamine is zein, gliadin or hordenin, or various mixtures thereof.

10. A dosage form as claimed in claim 1, wherein said proportions for tablets vary from about 100:17:4 to about 100:25:8.

11. A dosage form as claimed in claim 1, wherein said proportions for capsules vary from about 100:25:5 to about 100:35:7.

12. A process for the preparation of sustained release dosage forms, which consists in (a) mixing a pharmacologically effective substance with at least two members selected from a higher alkanol and alkanoic acid melting above 25° C, (b) heating the mixture to about 55°–65° C., c) granulating the resulting solid mixture with a solution of a prolamine, (d) evaporating the solvent of said solution and (e) compressing the resulting granules into tablets, or breaking said tablets and filling the resulting granules into capsules.

13. A process for the preparation of sustained release dosage forms, which consists in (a) mixing a pharmacologically effective substance with at least two members selected from a higher alkanol and alkanoic acid melting above 25° C., (b) granulating the resulting solid mixture with a solution of a prolamine, (c) evaporating the solvent of said solution and (d) compressing the resulting granules into tablets, or breaking said tablets and filling the resulting granules into capsules.

* * * * *